United States Patent [19]

Cella

[11] 4,257,957
[45] Mar. 24, 1981

[54] METHYL-TRIS-(4-HYDROXYCOUMARIN)-SILANE

[75] Inventor: James A. Cella, Clifton Park, N.Y.

[73] Assignee: General Electric Company, Schenectady, N.Y.

[21] Appl. No.: 104,425

[22] Filed: Dec. 17, 1979

Related U.S. Application Data

[62] Division of Ser. No. 927,288, Jul. 24, 1978, Pat. No. 4,210,596.

[51] Int. Cl.$^3$ ............................................. C07D 311/46
[52] U.S. Cl. .................................................. 260/343.44
[58] Field of Search .................................... 260/343.44

[56] References Cited

PUBLICATIONS

Steven Torkelson et al. Synthesis (1976) p. 722–724.
Hengge et al. Monatshefte für Chemie 104, 1071–1076, 1973.

Primary Examiner—John D. Randolph
Assistant Examiner—Jane T. Fan
Attorney, Agent, or Firm—William A. Teoli; James C. David, Jr.

[57] ABSTRACT

Silyl ethers of 1,3-dicarbonyl cyclic compounds, such as methyl tris-5,5-dimethyl-cyclohexen-2-one-3-yloxy silane can be made by effecting reaction in the presence of an acid acceptor between an organo halosilane and a 1,3-dicarbonyl cyclic organic compound, for example, 5,5-dimethyl-1,3-cyclohexane dione. The silyl ethers are useful as vulcanizing agents for silanol terminated polydiorganosiloxanes.

1 Claim, No Drawings

METHYL-TRIS-(4-HYDROXYCOUMARIN)SILANE

This is a division of application Ser. No. 927,288, filed July 24, 1978, now U.S. Pat. No. 4,210,596.

The present invention relates to certain silyl ethers of 1,3-dicarbonyl cyclic organic compounds and a method for making such materials.

The silyl ethers of the present invention have the formula,

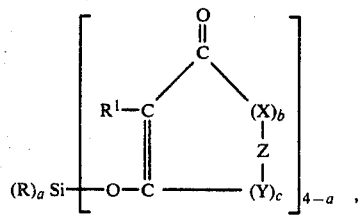
(1)

where R is a $C_{(1-13)}$ monovalent organic radical, $R^1$ is selected from hydrogen, halogen and R, X and Y are divalent radicals selected from —O—, —S—,

Z is a divalent $C_{(1-13)}$ organic radical selected from alkylene, cycloalkylene, arylene and a fused ring structure, b and c are equal to 0 or 1, $R^2$ is selected from hydrogen and R, and a is a whole number having a value of from 0 to 2 inclusive.

Radicals included by R of formula (1) are aryl radicals and halogenated aryl radicals, such as phenyl, chlorophenyl, xylyl, tolyl, etc.; aralkyl radicals, such as phenylethyl, benzyl, etc.; alkyl and alkenyl radicals, such as methyl, ethyl, propyl, chloromethyl, butyl, vinyl, etc.; cyclo alkyl, such as cyclohexyl, cycloheptyl, etc. In formula (1), where R is more than one radical, these radicals can be the same or different.

The silyl ethers of formula (1) can be made by effecting reaction under substantially anhydrous conditions between an organohalosilane of the formula,

(2)

where R and a are as previously defined and Q is a halogen radical, and a cyclic 1,3-dicarbonyl compound of the formula,

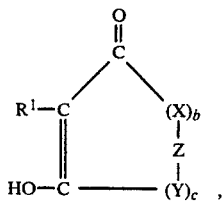
(3)

in the presence of a base catalyst where $R^1$, X, Y, Z, b and c are as previously defined. Preferably, the organohalosilane of formula (2) are alkyl halosilane of the formula,

(4)

where Q is as previously defined, and $R^3$ is a $C_{(4-12)}$ alkyl radical such as butyl, pentyl, hexyl, heptyl, octyl, nonyl, decyl, etc.

There are included by the organohalosilanes of formulas (2) and (4), methyltrichlorosilane, butyltrichlorosilane, phenyltrichlorosilane, n-hexylethyldichlorosilane, dodecyltrichlorosilane, trifluoropropyltrichlorosilane, tetrachlorosilane, etc.

There are included by the 1,3-dicarbonyl compound of formula (3), cyclohexane-1,3-dione, isopropylidene malonate, 3-hydroxycoumarin, 5,5-dimethylcyclohexane-1,3-dione, 2-methylcyclopentane-1,3-dione, 2-bromocyclohexane-1,3-dione, 5,5-dimethyl-3-ketovalerolactone, N-phenyl-3-ketobutyrolactam, etc.

In the practice of the invention, the silyl ethers of formula (1) can be made by effecting reaction under substantially anhydrous conditions between 1-4 mols of the 1,3-dione of formula (3), per mole of organohalosilane of formulas (2) or (4), to insure that there is at least a stoichiometric equivalent between the gram mols of hydroxy of the 1,3-dione and the halogen attached to the silicon of the organohalosilane.

Reaction between the 1,3-dione and the organosilane is usually effected in the presence of a basic acceptor, such as organic amine, for example, triethylamine, pyridine, etc. Sufficient base acceptor is utilized to completely neutralize any acid byproducts formed during the reaction. Reaction can be facilitated by use of a nonpolar neutral organic solvent, such as toluene, benzene, hexane, pentane, chloroform, etc., at temperatures in the range of from 0° C. to 150° C. During the reaction the mixture can be agitated such as by stirring, etc. The mixture then can be filtered of amine salts and the filtrate stripped of organic solvent.

In order that those skilled in the art will be better able to practice the invention, the following examples are given by way of illustration and not by way of limitation. All parts are by weight.

EXAMPLE 1

A solution of 15.1 parts of 2-methylcyclohexane-1,3-dione in about 500 parts of dry toluene was refluxed to effect the removal of water from the mixture by azeotropic distillation. There was added to the resulting solution, after it had been allowed to cool, about 15 parts of dry triethylamine followed by 7.3 parts of methyltrichlorosilane. The resulting mixture was then stirred for two hours. The mixture was filtered to effect the removal of triethylamine hydrochloride and then stripped of solvent. There was obtained 15.4 parts of a brown solid which was a yield of 95%. Based on method of preparation, the product was methyl-tris(2-methyl-1,3-cyclohexanedione)silane having the formula,

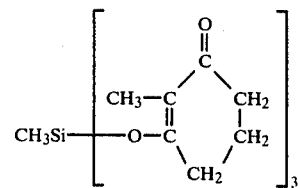

The identity of the product was further confirmed by its NMR spectrum.

A moisture curable organopolysiloxane composition was prepared by blending under substantially anhydrous conditions, 6 parts of the above 1,3-dicarbonylsilyl ether, 100 parts of a silanol-terminated polydimethylsiloxane having a viscosity of about 35,000 centipoises at 25° C. and a hydroxy content of 0.09% by weight, 20 parts of fumed silica and 0.05 part of dibutyltindilaurate. The organopolysiloxane composition was substantially odorless and cured to a tack-free state when it was allowed to rest under atmospheric conditions for about 2 hours. A complete cure was achieved in about 20 hours under atmospheric conditions. A copper substrate coated with the same moisture curable organopolysiloxane and held at 90% relative humidity for 2 weeks was found to be substantially free of corrosion.

EXAMPLE 2

The procedure of Example 1 was repeated, except that in place of 2-methylcyclohexane-1,3-dione, there was used cyclohexane-1,3-dione. Based on method of preparation, there was obtained a 1,3-dicarbonylsilyl ether of the formula,

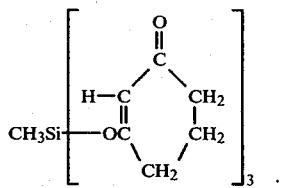

Its identity was confirmed with NMR.

It was found that the resulting moisture curable organopolysiloxane composition made in accordance with the procedure of Example 2, produced a substantially odorless, tack-free elastomer after 15 minutes exposure to atmospheric conditions, while a completely cured elastomeric product was obtained in only 3 hours.

EXAMPLE 3

There was added 151.25 parts of dodecyltrichlorosilane to a stirred solution of 210 parts of cyclohexan-1,3-dione and 156.5 parts of triethylamine in 3,140 parts of dry toluene. The mixture was stirred at reflux for 1 hour and filtered. There was obtained 263 parts of product representing an 86% yield. Based on method of preparation, the product was a 1,3-dicarbonylsilyl ether of the formula,

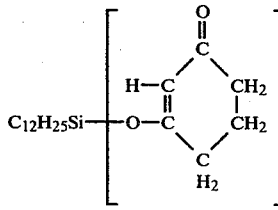

A mixture of 6 parts of the above 1,3-dicarbonylsilylether and 100 parts of silanol terminated polydimethylsiloxane was prepared as described in Example 1. The resulting room temperature vulcanizing composition was compared to the room temperature composition of Example 2 with respect to how long the mixtures were workable after being exposed to atmospheric conditions. The "work life" test was performed by allowing equal parts of the respective room temperature vulcanizing mixtures to rest under atmospheric conditions until the curable mixtures formed a skin while in an aluminum cup. The mixtures were then difficult to stir with a spatula. It was found that the work life of the mixture having chemically combined dodecyl siloxy units was about 3–5 minutes, while the worklife of the methyl-substituted siloxy containing 1,3-dicarbonyl units was approximately 0.5 to 1 minute. This work life test showed that the 1,3-dicarbonylsilylether silane advantageously extended the period of use of the resulting room temperature vulcanizing mixture.

EXAMPLE 4

There was added 50 parts of methyltrichlorosilane to a mixture of 100 parts of triethylamine, 162 parts of 4-hydroxycoumarin and about 2,100 parts of dry toluene. When the dropwise addition was completed, the mixture was filtered and the filtrate was stripped of toluene. There was obtained 170 parts of methyl-tris(4-hydroxycoumarin)silane having the formula,

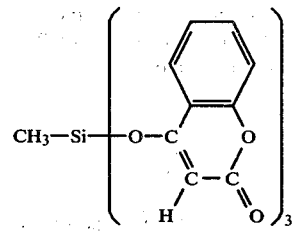

The identity of the above methyl-tris-1,3-dicarbonylsilane was further confirmed by its NMR spectrum.

A blend of 5 parts of the silane and 100 parts of silanol-terminated polydimethylsiloxane and 1 part of dibutyltindilaurate formed a tack-free elastomer after about 1 hour exposure to atmospheric conditions.

Although the above examples are directed to only a few of the very many variables which can be used to make the 1,3-dicarbonylsilanes of the present invention, it should be understood that the method of the present invention as well as the compounds obtained thereby can be practiced in accordance with the description shown in the specification prior to these examples, such as the use of silanes of formulas (2) or (4) and 1,3-dicarbonyl compounds of formula (3). Accordingly, there are also preferably included by the present invention, silyl ethers of 1,3-dicarbonyl cyclic compounds having the formula,

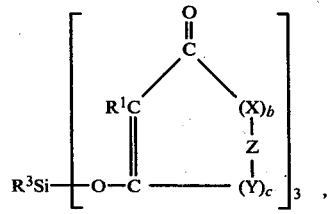

where $R^1$, $R^3$, b and c are as previously defined.

In addition to the above described silyl ethers of 1,3-dicarbonyl cyclic compounds of the present invention, certain alkoxy-substituted 1,3-dicarbonyl cyclic compounds and moisture curable organopolysiloxane compositions are also shown in the applications Ser. No. 927,287, filed July 24, 1978 and Ser. No. 927,284, filed July 24, 1978, now U.S. Pat. No. 4,176,112 of James A. Cella and Tyrone D. Mitchell, assigned to the same assignee as the present invention.
What I claim as new and desire to secure by Letters Patent of the United States is:
1. The compound
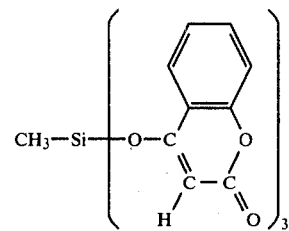
* * * * *